(12) United States Patent
Rutka et al.

(10) Patent No.: US 10,413,552 B2
(45) Date of Patent: Sep. 17, 2019

(54) METHOD OF TREATING MEDULLOBLASTOMA

(71) Applicant: THE HOSPITAL FOR SICK CHILDREN, Toronto (CA)

(72) Inventors: James Rutka, Toronto (CA); Claudia Faria, Toronto (CA)

(73) Assignee: The Hospital for Sick Children, Toronto (CA)

( * ) Notice: Subject to any disclaimer, the term of this patent is extended or adjusted under 35 U.S.C. 154(b) by 0 days.

(21) Appl. No.: 15/737,626

(22) PCT Filed: Jun. 17, 2016

(86) PCT No.: PCT/CA2016/050713
§ 371 (c)(1),
(2) Date: Dec. 18, 2017

(87) PCT Pub. No.: WO2016/201581
PCT Pub. Date: Dec. 22, 2016

(65) Prior Publication Data
US 2018/0185381 A1    Jul. 5, 2018

Related U.S. Application Data

(60) Provisional application No. 62/181,630, filed on Jun. 18, 2015.

(51) Int. Cl.
*A61K 31/55* (2006.01)
*A61P 35/00* (2006.01)

(52) U.S. Cl.
CPC .............. *A61K 31/55* (2013.01); *A61P 35/00* (2018.01)

(58) Field of Classification Search
CPC .............................. A61K 31/55; A61P 35/00
See application file for complete search history.

(56) References Cited

U.S. PATENT DOCUMENTS 7,232,814 B2    6/2007 Meijer et al.
8,431,522 B2    4/2013 Costa et al.
(Continued)

FOREIGN PATENT DOCUMENTS

EP         1616568 A2    1/2006
WO    WO2012/136851 A1   10/2012

OTHER PUBLICATIONS

Kuzan-Fischer et al. (J Korean Neurosurg Soc 61 (3) oages 292-301, 2018).*

(Continued)

*Primary Examiner* — Savitha M Rao
(74) *Attorney, Agent, or Firm* — Milstein Zhang & Wu LLC (57) ABSTRACT

A method of treating a medulloblastoma in a mammal is provided comprising administering to the mammal a compound having the following general formula (1): wherein X is selected from the group consisting of hydrogen, hydroxyl (—OH), halogen, thio (—SH), sulfanyl (—SR), sulfinyl (—SOR), sulfonyl (—SO$_2$R), carboxyl (—COOH), carbonyl (COOR), nitro (—NO$_2$), nitroso (—NOR), amino (NH$_2$), NHR, NRR1, cyano (—CN) and isocyano (—NC), wherein R and R1 are independently C$_1$-C$_5$ branched or unbranched lower alkyl; and Y is a 5- or 6-membered unsaturated ring, optionally substituted, or a pharmaceutically acceptable salt thereof.

(Continued)

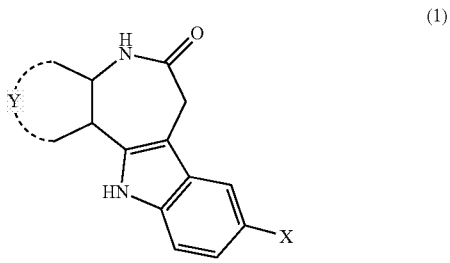

(1)

2 Claims, 3 Drawing Sheets (56) References Cited

U.S. PATENT DOCUMENTS

2012/0010178 A1* 1/2012 Rubin .................. A61K 31/17
514/158
2014/0234271 A1 8/2014 Miller et al.

OTHER PUBLICATIONS

Faria, et al. (2012) Identification of Alsterpaullone as a Novel Small Molecule Inhibitor to Target Group 3 Medulloblastoma, Oncotarget vol. 6, 25, pp. 21718-21729.
PCT/CA2016/050713, Int'l Search Report, dated Aug. 30, 2016.
PCT/CA2016/050713, Written Opinion of the ISA, dated Aug. 30, 2016.

* cited by examiner

METHOD OF TREATING MEDULLOBLASTOMA

RELATED APPLICATIONS

This application is the U.S. national phase of and claims priority to PCT/CA2016/050713, filed Jun. 17, 2016, which claims the benefit of priority to U.S. Provisional Application Ser. No. 62/181,630, filed on Jun. 18, 2015, the entire content of each of which is incorporated herein by reference for all purposes.

FIELD OF THE INVENTION

The present invention relates to a method of treating medulloblastoma.

BACKGROUND OF THE INVENTION

Medulloblastoma is the most common malignant pediatric brain tumor consisting of at least four distinct molecular subgroups: Wingless (WNT), sonic hedgehog (SHH), Group 3 and Group 4. These subgroups are characterized by divergent genetic aberrations, cytogenetic features, and distinct phenotypes including patient demographics and clinical outcome. Tumors with WNT pathway activation have the most favorable prognosis whereas Group 3 medulloblastomas have the worst outcome. Group 3 tumors are restricted to pediatric patients, characterized by amplification of MYC (a regulator gene encoding a transcription factor), and are frequently metastatic at the time of diagnosis. These tumors are particularly resistant to conventional therapies with radiation and chemotherapy, even at maximally tolerated doses, highlighting the need for novel and more effective therapeutic options.

It would be desirable, thus, to develop a therapy useful to treat a medulloblastoma.

SUMMARY OF THE INVENTION

Small molecule inhibitors have now been identified which are useful to treat medulloblastomas.

Thus, in one aspect, a method of treating a medulloblastoma in a mammal is provided comprising administering to the mammal a compound having the following general formula:

Formula 1 wherein X is selected from the group consisting of hydrogen, hydroxyl (—OH), halogen (e.g. Br, Cl, F and I), thio (—SH), sulfanyl (—SR), sulfinyl (—SOR), sulfonyl (—SO$_2$R), carboxyl (—COOH), carbonyl (—COOR), nitro (—NO$_2$), nitroso (—NOR), amino (—NH$_2$), NHR, NRR1, cyano (—CN) and isocyano (—NC), wherein R and R1 are independently C$_1$-C$_5$ lower branched or unbranched alkyl; and Y is a 5- or 6-membered unsaturated ring, optionally substituted, including pharmaceutically acceptable salts thereof.

In another aspect of the present invention, a composition is provided comprising a compound having the following general formula:

Formula 1 in combination with a second therapeutic compound for treating a medulloblastoma.

These and other aspects of the invention will become apparent by reference to the detailed description and figures.

BRIEF DESCRIPTION OF THE FIGURES

FIG. 2. Piperlongumine (PL), alsterpaullone (ALP) and rottlerin (RTL) reduce tumor growth and increase survival in medulloblastoma xenografts as shown by: a) Representative bioluminescence imaging of D458 cerebellar xenografts treated with vehicle control (10% DMSO, n=14), PL (50 mg/kg, s.c., daily for 2 weeks; n=10), ALP (30 mg/kg, s.c., daily for 2 weeks; n=14) and RTL (20 mg/kg, s.c., every other day for 2 weeks; n=11); b) Connectivity Map which predicted drugs reduce medulloblastoma growth as denoted by a smaller change in total photon flux. Data represent group means±SEM; and c-e) Kaplan-Meier survival curves which demonstrate that mice harboring orthotopic D458 medulloblastoma xenografts have an increased survival after treatment with PL (p=0.0011), ALP (p=0.0043) and RTL (p=0.0262). Survival differences were calculated using a log-rank test.

DETAILED DESCRIPTION OF THE INVENTION

A method of treating a medulloblastoma in a mammal is provided comprising administering to the mammal a compound having the following general formula:

Formula 1 wherein X is selected from the group consisting of hydrogen, hydroxyl (—OH), halogen (e.g. Br, Cl, F and I), thio (—SH), sulfanyl (—SR), sulfinyl (—SOR), sulfonyl (—SO$_2$R), carboxyl (—COOH), carbonyl (—COOR), nitro (—NO$_2$), nitroso (—NOR), amino (NH$_2$), NHR, NRR1, cyano (—CN) and isocyano (—NC), wherein R and R1 are independently C$_1$-C$_5$ branched or unbranched lower alkyl; and Y is a 5- or 6-membered unsaturated ring, optionally substituted with, for example, hydroxyl (—OH), halogen (e.g. Br, Cl, F and I), thio (—SH), cyano (CN), nitro (—NO$_2$), amino, and C$_1$-C$_5$ lower alkyl.

Y may be benzene, furan, pyrrole, thiophene, pyrazole, imidazole, oxazole, isoxazole, thiazole, isothiazole, pyran, thiopyran, pyridine, pyran, pyrazine, pyrimidine, pyridazine, diazine, oxazine, thiazin, dioxine or dithiine, optionally substituted as above.

Y is preferably benzene or pyridine.

In one embodiment, the compound may be a substituted or unsubstituted paullone compound that is a cyclin-dependent kinase (CDK) inhibitor and/or a glycogen synthase kinase (GSK)-3β inhibitor. Examples of suitable paullone compounds include, but are not limited to, paullone, 9-nitro-7,12-dihydroindolo-[3,2-d][1]benzazepin-6(5)-one (alsterpaullone), 9-cyano-1-azapaullone (cazpaullone) and 9-Bromo-7,12-dihydro-indolo[3,2-d][1]benzazepin-6(5H)-one (kenpaullone).

As one of skill in the art will appreciate, the substituted paullone compound may also be used in accordance with the invention, as a pharmaceutically acceptable salt. A "pharmaceutically acceptable salt" refers to a salt that retains the desired biological activity of the parent compound and does not impart unacceptable toxicological or other effects. Examples of such salts include acid addition salts and base addition salts. Acid addition salts include those derived from non-toxic inorganic acids, such as hydrochloric, nitric, phosphoric, sulfuric, hydrobromic, hydroiodic, phosphorous and the like, as well as those derived from non-toxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from non-toxic organic amines, such as N,N'-dibenzylethylenediamine, N-methylglucamine, chloroprocaine, choline, diethanolamine, ethylenediamine, procaine and the like.

The present compounds may be obtained using standard chemical synthetic methods. Many of the compounds are also commercially available.

The present compounds may be formulated for therapeutic use by combination with a pharmaceutically acceptable carrier. The expression "pharmaceutically acceptable" means acceptable for use in the pharmaceutical and veterinary arts, i.e. not being unacceptably toxic or otherwise unsuitable. As one of skill in the art will appreciate, the selected carrier will vary with intended utility of the formulation. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule, lozenge, solution or suspension in an aqueous or non-aqueous liquid, an oil-in-water or water-in-oil liquid emulsion, an elixir or syrup are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragacanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and/or phosphate buffered solutions. Wetting agents, lubricants such as sodium lauryl sulfate, stabilizers, tableting agents, disintegrating agents, colouring agents and flavouring agents may also be present. In another embodiment, the composition may be formulated for application topically as a cream, lotion or ointment. For such topical application, the composition may include an appropriate base such as a triglyceride base. Such creams, lotions and ointments may also contain a surface active agent and other cosmetic additives such as skin softeners and the like as well as fragrance. Aerosol formulations, for example, for nasal delivery, may also be prepared in which suitable propellant adjuvants are used. Compositions of the present invention may also be administered as a bolus, electuary, or paste. Compositions for mucosal administration are also encompassed, including oral, nasal, rectal or vaginal administration for the treatment of infections which affect these areas. Such compositions generally include one or more suitable non-irritating excipients or carriers comprising, for example, cocoa butter, polyethylene glycol, a suppository wax, a salicylate or other suitable carriers. Other adjuvants may also be added to the composition regardless of how it is to be administered which, for example, may aid to extend the shelf-life thereof, including antioxidants, preservatives and anti-microbial agents.

The present compound, or composition, is used in a method of treating medulloblastoma in a mammal. The terms "treat", "treating" or "treatment" are used herein to refer to methods that favourably alter the medulloblastoma, including those that moderate, reverse, reduce the severity of, or protect against, the progression of the medulloblastoma. The term "medulloblastoma" refers to a malignant tumour in the cerebellum, including at least one of the main subgroups, WNT (DKK1 positive), SHH (SFRP1 positive), Group 3 (NPR3 positive) and Group 4 (KCNA1 positive) medulloblastomas.

The term "mammal" is used herein to refer to both human and non-human mammals.

According to the present method, the selected compound of formula 1, or composition comprising the compound, may be administered to a mammal in need of treatment via one or more routes of administration using one or more of a variety of methods known in the art. As will be appreciated by the skilled artisan, the route and/or mode of administration will vary depending upon the desired results. Preferred routes of administration include parental routes, such as intravenous, intramuscular, intradermal, intraperitoneal, subcutaneous, spinal, intraarterial, intrathecal, intracapsular, intraorbital, intracardiac, transtracheal, subcuticular, intraarticular, subcapsular, subarachnoid, intraspinal, epidural and intrasternal injection and infusion. Alternatively, non-parenteral routes of administering a compound, including topical, epidermal or mucosal routes of administration, for example, intranasally, orally, vaginally, rectally, sublingually or topically, may be utilized.

The selected compound is administered to a mammal in the treatment of medulloblastoma in an amount sufficient to treat the medulloblastoma. In this regard, dosages in the range of about 1-100 mg/kg body weight, for example, 25-35 mg/kg body weight will typically be effective. As one of skill in the art will appreciate, the effective dosage will vary with the selected compound, the mammal being treated and the medulloblastoma subtype being treated, and thus, dosages outside of this range may also be effective, including dosages in the range of about 0.1-1000 mg/kg body weight.

As one of skill in the art will appreciate, the present compounds may be administered in conjunction with (e.g. either simultaneously, separately or in combination, or at different times) one or more additional therapeutics useful to treat a medulloblastoma, such as cisplatin, carboplatin, cyclophosphamide, and vincristine, or therapies useful to treat the symptoms of medulloblastoma, such as pain medication. The present compounds may also be used in conjunction with appropriate additional treatments, such as radiation.

Embodiments of the invention are described in the following example which is not to be construed as limiting.

Example 1

Materials and Methods

The subgroup-specific gene expression profiles of primary medulloblastomas were obtained from previously published datasets {Northcott et al., J Clin Oncol. 2011. 29:1408}. A list of genes differentially expressed between each medulloblastoma subgroup and normal cerebellum was obtained and the top 200 up- and down-regulated genes were selected to query the Connectivity Map analysis (C-MAP) database. Compounds with a negative enrichment score, which implies the ability to reverse the direction of expression of the gene signature of interest, and a p-value inferior to 0.05, were recorded as potential therapeutic agents for medulloblastoma {Lamb et al. Science, 2006. 313:1929; Lamb, Nat Rev Cancer, 2007. 7:54}.

Medulloblastoma Cell Lines

The medulloblastoma cell lines (D425 and D458) were kindly provided by Dr. Annie Huang, Hospital for Sick Children, Toronto, Canada. D458-GFP/Luciferase cells were generated as described previously {Diaz et al. J Neurooncol, 2012. 108:349}.

Cell Proliferation Assays

D425 and D458 cells were grown as suspension cultures and seeded in 96-well microplates at 10,000 cells per well. Fetal normal human brain cells (hf5281) were grown as an adherent culture and seeded in 96-well microplates at 4,000 and 5,000 cells per well. Cells were treated for 48 h with different concentrations of Piperlongumine (PL; INDOFINE Chemical Company), alsterpaullone (ALP; A. G. Scientific), rottlerin (RTL; A. G. Scientific) and flunarizine (FZ; Sigma) or DMSO (control). Cell viability was determined by MTS proliferation assay (3-(4,5-dimethylthiazol-2-yl)-5-(3-carboxymethoxyphenyl)-2-(4-sulfophenyl)-2H-tetrazolium) and the absorbance was measured at 490 nm (CellTiter 96 Aqueous One Solution Reagent; Promega). Three independent experiments were performed with 16 repeats per treatment condition.

All mouse studies were approved by the Institutional Animal Care and Use Committee of the University of Toronto and the Hospital for Sick Children, in Toronto, and performed in accordance with their policies and regulations.

Medulloblastoma Xenografts

Medulloblastoma intracranial xenografts were established in 5-6 week old athymic nude mice (Charles River Laboratories). Medulloblastoma cells (250,000 D425 and D458 cells) were implanted in the right cerebellum of mice. Six days after cell inoculation, animals were randomized into treatment cohorts, which included subcutaneous injections with vehicle control (10% DMSO), PL (50 mg/kg, daily for 2 weeks), ALP (30 mg/kg, daily for 2 weeks), RTL (20 mg/kg, every other day for 2 weeks) or FZ (50 mg/Kg, daily for 2 weeks).

In animals bearing D458-GFP/Luciferase xenografts, bioluminescence imaging was performed at 6 days after intracranial injection. Mice with a detectable signal were included in the study and tumor growth was monitored at one-week intervals using the IVIS Spectrum Optical In-vivo Imaging System (Caliper Life Sciences).

Animals with progressive neurological signs or weight loss greater than 20% were euthanized and the brains harvested and fixed in 10% formalin.

Immunoblotting

Cell lysates were prepared by adding RIPA buffer (Sigma) containing protease inhibitors (F. Hoffman-La Roche AG), 0.2 M sodium orthovanadate, 0.2 M sodium pyrophosphate and 0.2 M sodium fluoride. The Pierce BCA Protein Assay Kit (Thermo Scientific) was used to determine protein concentration. Proteins were separated on 7.5% or 10% SDS-PAGE gels and transferred to PVDF membranes using a semi-dry transfer apparatus (Bio-Rad). The following antibodies were used: PARP (1:1,000; Cell Signaling), AKT (1:1,000; Cell Signaling), phospho-AKT (1:2,000; Ser473, Cell Signaling), α-tubulin (1:1,000; Cell Signaling), anti-mouse IgG conjugated to horseradish peroxidase (1:5,000; Amersham Biosciences) and anti-rabbit IgG conjugated to horseradish peroxidase (1:5,000; Cell Signaling).

RNA Extraction and Gene Expression Analysis

D425 and D458 medulloblastoma cells were treated with 5 μM of PL, 5 μM of ALP or DMSO (control) for 48 h. RNA isolation was performed using the RNeasy Mini Kit (Qiagen) and gene expression data were generated using the Human PrimeView Arrays. Gene Set Enrichment Analysis (GSEA) was performed using gene sets from the National Cancer Institute (NCI), Gene Ontology (GO), Kyoto Encyclopedia of Genes and Genomes (KEGG), Protein Families (PFAM) and Biocarta pathway databases. Significant gene sets were identified (FDR<0.05; p<0.01) and visualized in Cytoscape and Enrichment Map software.

A list of genes up- and down-regulated by ALP in D425 and D458 medulloblastoma cells was generated. The top 200 genes were selected to query the C-MAP database and to determine if alsterpaullone and piperlongumine were able to reverse the gene expression profile of Group 3 medulloblastoma cells (p<0.05).

Statistical Analysis

The Kaplan-Meier estimate and a log-rank test were used to generate survival curves. Experiments were performed in triplicate and results were expressed as mean±SEM. Statistical analysis was performed using GraphPad Prism 5 Software. A p-value inferior to 0.05 was considered as significant.

Results

To identify novel drugs with potential antitumor effect in medulloblastoma, the C-MAP database was queried using the previously published gene expression signatures of the four molecular subgroups of medulloblastoma {Northcott, J Clin Oncol. 2011. 29; 1408}. The top 20 drugs that were able to reverse the gene expression profile of each medulloblastoma subgroup are listed in Table 1.

TABLE 1

| Rank | C-MAP Name | Enrichment | Rank | C-MAP Name | Enrichment |
|---|---|---|---|---|---|
| WNT | | | SHH | | |
| 9 | monobenzone | −0.855 | 66 | piperlongumine | −0.919 |
| 24 | chrysin | −0.841 | 20 | trazodone | −0.916 |
| 5 | hexamethonium bromide | −0.806 | 4 | luteolin | −0.915 |
| | | | 5 | phenoxybenzamine | −0.909 |
| 13 | simvastatin | −0.805 | 8 | apigenin | −0.899 |
| 14 | pimozide | −0.805 | 10 | Prestwick-1084 | −0.897 |
| 8 | astemizole | −0.796 | 117 | DL-thiorphan | −0.869 |
| 10 | antimycin A | −0.787 | 18 | bepridil | −0.856 |
| 43 | reserpine | −0.786 | 54 | chrysin | −0.834 |
| 46 | etacrynic acid | −0.783 | 56 | ronidazole | −0.833 |
| 19 | methylprednisolone | −0.774 | 23 | thiostrepton | −0.831 |
| 20 | chlorphenesin | −0.772 | 25 | puromycin | −0.830 |
| 11 | pyrimethamine | −0.763 | 29 | repaglinide | −0.809 |
| 12 | halcinonide | −0.746 | 79 | 0297417-0002B | −0.803 |
| 25 | aminophylline | −0.745 | 31 | GW-8510 | −0.797 |
| 61 | esculetin | −0.745 | 33 | monobenzone | −0.795 |
| 26 | 3-nitropropionic acid | −0.743 | 87 | etacrynic acid | −0.789 |
| | | | 39 | thioguanosine | −0.780 |
| 29 | etoposide | −0.724 | 40 | cyproterone | −0.780 |
| 3 | methotrexate | −0.723 | 43 | sulconazole | −0.766 |
| 30 | semustine | −0.722 | | | |
| 31 | parthenolide | −0.720 | | | |
| 33 | lomustine | −0.708 | | | |
| Group 3 | | | Group 4 | | |
| 3 | phenoxybenzamine | −0.957 | 12 | piperlongumine | −0.971 |
| 28 | piperlongumine | −0.950 | 1 | phenoxybenzamine | −0.930 |
| 93 | 1,4-chrysenequinone | −0.892 | 13 | etacrynic acid | −0.902 |
| | | | 92 | 1,4-chrysenequinone | −0.896 |
| 101 | DL-thiorphan | −0.885 | | | |
| 11 | monobenzone | −0.841 | 28 | chrysin | −0.865 |
| 13 | carbachol | −0.833 | 51 | 0297417-0002B | −0.825 |
| 47 | doxorubicin | −0.833 | 14 | apigenin | −0.815 |
| 14 | puromycin | −0.828 | 63 | Prestwick-559 | −0.811 |
| 51 | etacrynic acid | −0.828 | 16 | tyloxapol | −0.810 |
| 16 | imipenem | −0.815 | 64 | doxyrubicin | −0.809 |
| 63 | chrysin | −0.807 | 17 | imipenem | −0.808 |
| 18 | luteolin | −0.801 | 70 | ronidazole | −0.803 |
| 19 | trifluridine | −0.797 | 21 | Prestwick-1084 | −0.801 |
| 21 | GW-8510 | −0.796 | 34 | sulconazole | −0.771 |
| 72 | 0297417-0002B | −0.793 | 6 | levonorgestrel | −0.759 |
| 2 | resveratrol | −0.785 | 111 | milrinone | −0.759 |
| 7 | levonorgestrel | −0.779 | 38 | protriptyline | −0.754 |
| 90 | alsterpaullone | −0.777 | 41 | GW-8510 | −0.750 |
| 30 | metyrapone | −0.771 | 43 | metyrapone | −0.747 |
| 9 | medrysone | −0.770 | 44 | sulfametoxydiazine | −0.746 |

PL, a natural product derived from the plant species *Piper longum*, was the compound with the highest negative enrichment score for non-WNT (SHH) medulloblastomas. The compounds identified as potential novel therapies for WNT medulloblastomas are distinct from the ones identified for non-WNT tumors. On the other hand, the drugs listed for Group 3 and Group 4 tumors are very similar. Compounds specific for Group 3 medulloblastomas were then queried. On top of the list, a CDK inhibitor (ALP), a protein kinase C (PKC) inhibitor (rottlerin) and two calcium channel inhibitors (denatonium benzoate and flunarizine) showed significant negative enrichment (Table 2).

TABLE 2

| Rank | C-MAP name | Enrichment | Drug category |
|---|---|---|---|
| 96 | alsterpaullone | −0.765 | CDK inhibitor |
| 130 | rottlerin | −0.725 | PKC inhibitor |
| 69 | denatonium benzoate | −0.701 | calcium channel inhibitor |

TABLE 2-continued

| Rank | C-MAP name | Enrichment | Drug category |
|---|---|---|---|
| 104 | flunarizine | −0.664 | calcium channel inhibitor |
| 107 | bupropion | −0.661 | dopamine receptor antagonist |
| 117 | pyridoxine | −0.651 | pyridoxal kinase agonist |
| 31 | flunisolide | −0.644 | phospholipase A2 inhibitor |
| 125 | etamsylate | −0.643 | prostaglandin inhibitor |
| 135 | prenylamine | −0.635 | calcium channel inhibitor |
| 139 | practolol | −0.631 | beta-adrenergic antagonist |
| 140 | betaxolol | −0.629 | beta-adrenergic antagonist |

TABLE 2-continued

| Rank | C-MAP name | Enrichment | Drug category |
|---|---|---|---|
| 144 | propylthiouracil | −0.626 | thyroid peroxidase inhibitor |
| 136 | lorglumide | −0.57 | colecystokinin antagonist |
| 138 | amiodarone | −0.569 | calcium channel inhibitor |
| 113 | PNU-0251126 | −0.549 | not assessed |

Figure 1:
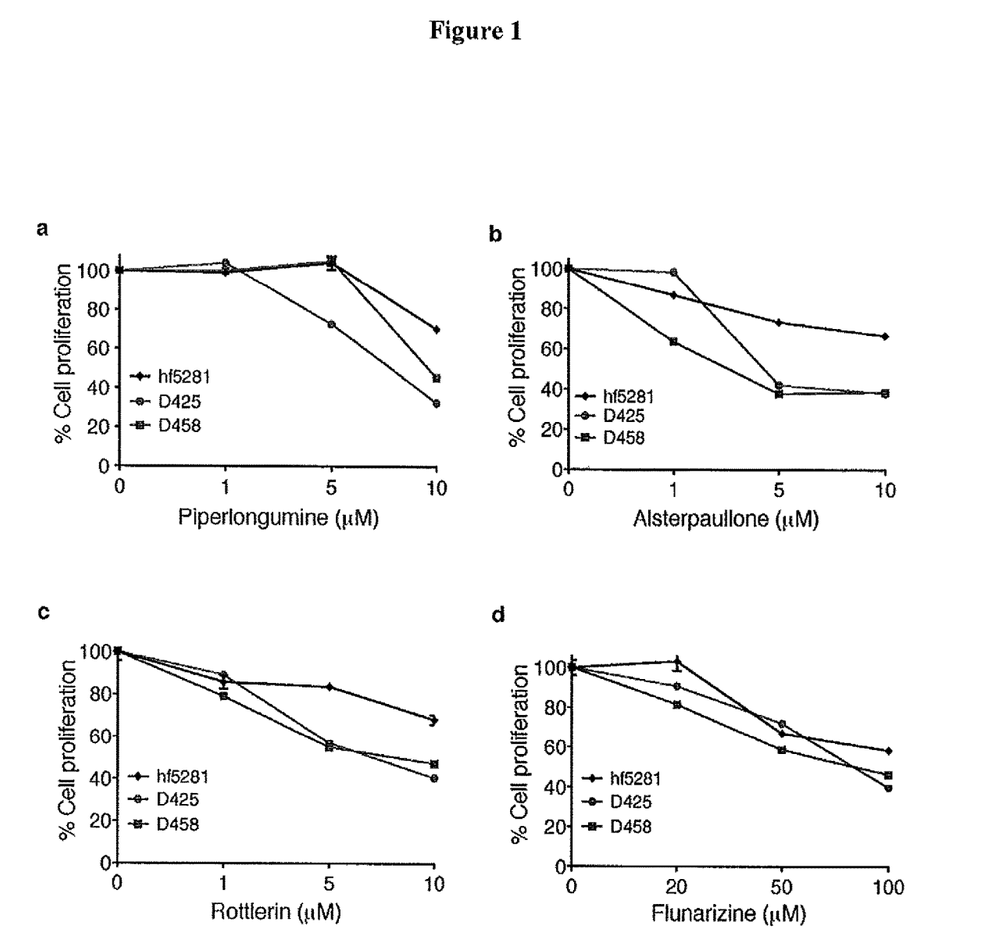
FIG. 1 illustrates the cytotoxic effect of piperlongumine, alsterpaullone, rottlerin and flunarizine in Group 3 medulloblastoma cell lines. Established medulloblastoma cell lines (D425 and D458) and a fetal neural stem cell line (hf5281) were treated with various concentrations of (a) piperlongumine, (b) alsterpaullone, (c) rottlerin and (d) flunarizine for 48 hours. Cell viability was measured by MTS assay. Data represent mean of triplicates±SEM.

NOTE:
The compounds were ranked based on negative enrichment score.
CDK, cyclin-dependent kinase;
PKC, protein kinase C To validate the results of the C-MAP analysis, PL (the best candidate for non-WNT medulloblastomas) and the top three drugs predicted to be specific for Group 3 medulloblastomas (alsterpaullone, rottlerin and flunarizine) were selected. The effects of each drug on the proliferation of two Group 3 medulloblastoma cell lines, D425 and D458, and a fetal normal human brain culture (hf5281) were determined. PL and rottlerin (RTL) treatment for 48 hours reduced cell proliferation in medulloblastoma cells at 5 µM (FIGS. 1a and 1c), whereas ALP treatment showed the same efficacy at 1 µM (FIG. 1b). Treatment with FZ decreased cell proliferation at higher concentrations (50 and 100 µM) (FIG. 1d). When normal human brain cells (hf5281) were incubated with PL, ALP and RTL there was little reduction in cell proliferation, even at the highest concentration tested of 10 µM, thus indicating that these compounds have selective killing properties to medulloblastoma tumor cells.

In Vivo Antitumor Effect in Group 3 Medulloblastomas

Figure 2:
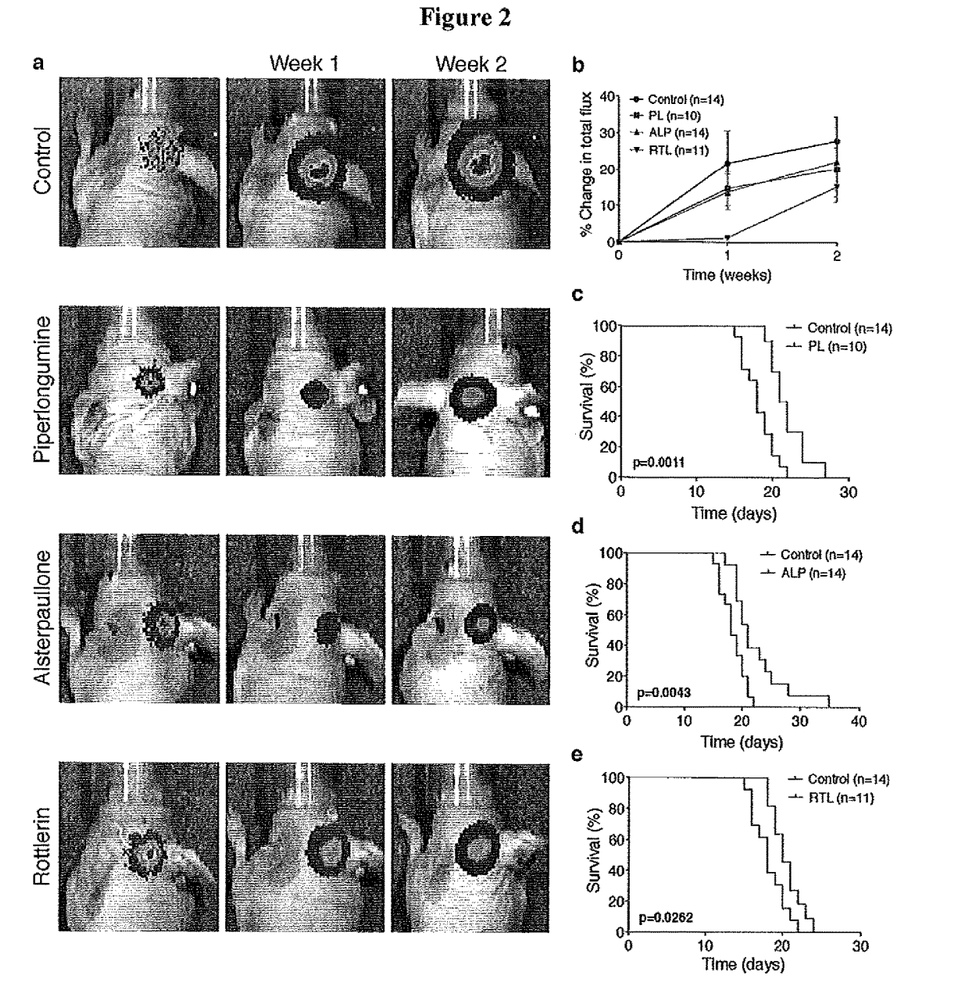

The efficacy of PL, ALP, RTL and FZ in established medulloblastoma xenografts representative of Group 3 medulloblastomas was then determined. D458 cells expressing luciferase were implanted in the right cerebellum of nude mice and bioluminescence imaging was performed at 6 days post inoculation. Animals with a detectable signal were treated by subcutaneous injection with PL (50 mg/kg, daily for 2 weeks), ALP (30 mg/kg, daily for 2 weeks), RTL (20 mg/kg, every other day for 2 weeks), FZ (50 mg/Kg, daily for 2 weeks) or vehicle control (10% DMSO). Marked reduction in medulloblastoma growth was observed in mice treated with PL, ALP and RTL when compared to DMSO-treated controls, as confirmed by bioluminescence imaging (FIGS. 2a and 2b) and by histological examination (H&E stain) of the brains. A significant increase in survival was also seen in mice treated with PL (FIG. 2c; p=0.0011), ALP (FIG. 2d; p=0.0043) and RTL (FIG. 2e; p=0.0262). As expected by the in vitro effects of FZ in cell proliferation, only seen at very high concentrations, this drug was not able to prolong survival of mice bearing medulloblastoma xenografts.

Figure 3:
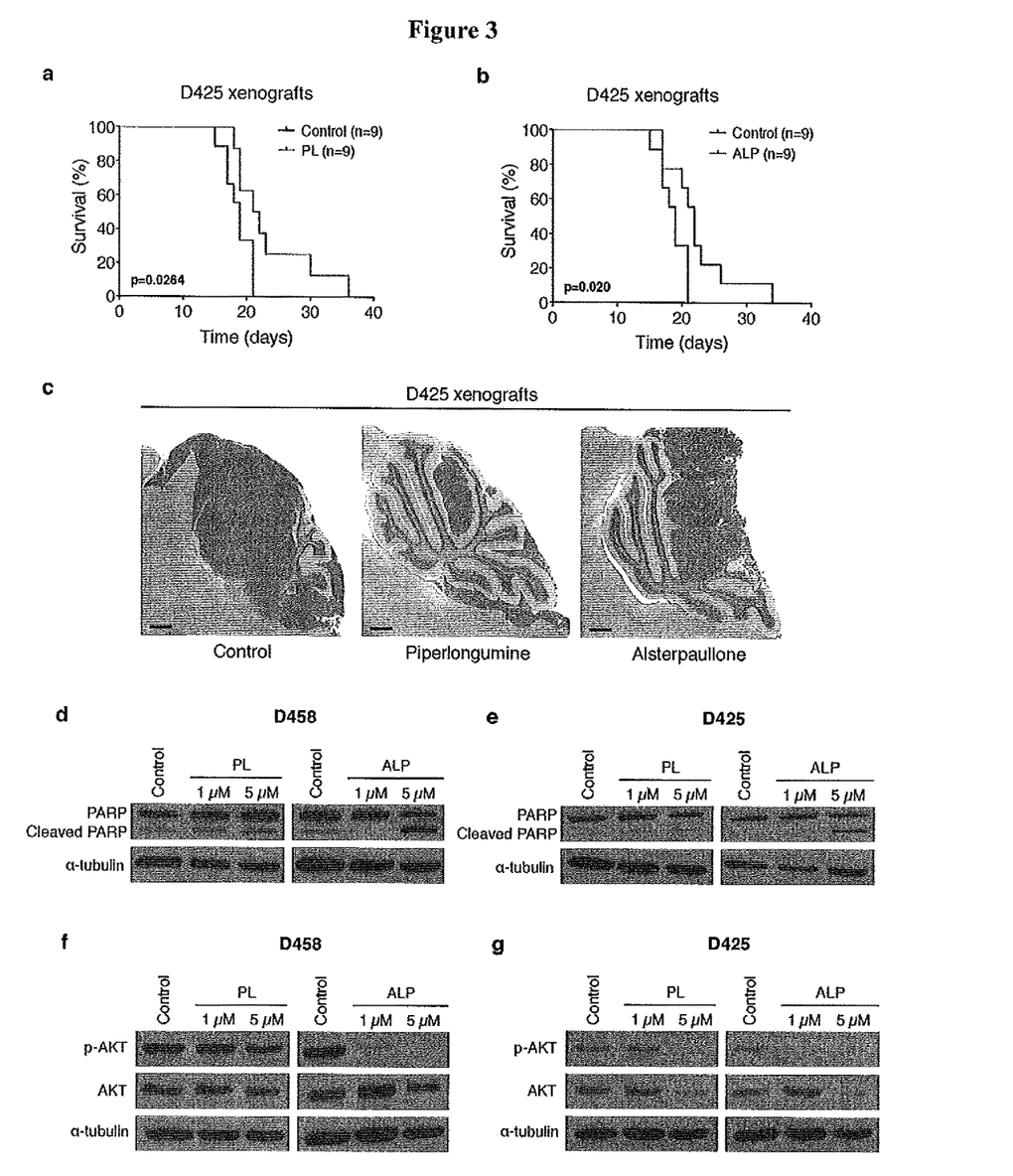
FIG. 3 illustrates Kaplan-Meier curves that display survival of nude mice with D425 cerebellar xenografts treated with (a) piperlongumine (PL) or (b) alsterpaullone (ALP). Survival differences were calculated using a log-rank test; (c) Representative H&E staining demonstrates reduction in medulloblastoma growth after treatment with PL and ALP, when compared to the control group. Scale bar: 500 µm; Representative Western blots demonstrating (d and e) induction of apoptosis and (f and g) AKT pathway inhibition after piperlongumine (PL) and alsterpaullone (ALP) treatment for 48 h in D458 and D425 medulloblastoma cells.

The two most promising drugs, PL and ALP, were then tested in nude mice with D425 cerebellar xenografts and both drugs were shown to significantly increase survival (FIGS. 3a and 3b; p<0.05) and reduce medulloblastoma growth (FIG. 3c). Collectively, these results confirm that the C-MAP top predicted drugs for Group 3 medulloblastomas are effective in treating medulloblastoma disease.

To determine the mechanisms by which PL and ALP exert their antitumor effect, D425 and D458 medulloblastoma cells were treated with both drugs for 48 h. Apoptosis and AKT pathway inhibition was assessed. Western blot analysis showed that ALP induced apoptosis (FIGS. 3d and 3e) and potently inhibited AKT pathway activation at lower concentrations than PL (FIGS. 3f and 3g).

Alsterpaullone Inhibits MYC and Other Cell Cycle Related Genes

To identify downstream transcriptional events induced by ALP, genomic profiling of Group 3 medulloblastoma cell lines (D425 and D458) was conducted after treatment for 48 hours. When compared to DMSO-treated medulloblastoma cells, ALP treated cells showed down-regulation of genes involved in cell cycle, including MYC, CDK7, RB1, CDK6, CCNB1, CDK5RAP2, CDK1 and CDKN2C. Gene Set Enrichment Analysis (GSEA) was performed with gene sets compiled from the National Cancer Institute (NCI), Gene Ontology (GO), Kyoto Encyclopedia of Genes and Genomes (KEGG), Protein Families (PFAM) and Biocarta pathway databases. To visualize significant gene sets (FDR<0.05; p<0.01) as interaction networks, Cytoscape and Enrichment Map were used. The top-scoring gene sets down-regulated by ALP were mainly cell cycle-related transcriptional signatures. In addition, ALP also inhibits several cancer-related networks (namely MTOR signaling, PTEN signaling, RAS signaling, Aurora kinase signaling, insulin signaling) and other biological processes including RNA processing, transport and splicing, DNA repair, chromatin organization and histone modifications, carbon metabolism and phosphatase activity. Gene sets up-regulated by ALP involve the inflammatory response (TNF signaling, MHC antigen presentation) and tissue regeneration (wound response and coagulation cascade, tissue morphogenesis, muscle contraction), as well as olfactory signaling, STAT signaling, alkene metabolism, lipid transport and neuropeptide receptor activity as shown in Table 3.

TABLE 3

| GSEA enriched pathway | Regulation | Rank | FDR-corrected (q value) |
|---|---|---|---|
| Systemic Lupus Erythematosus | Up-Regulated | 1 | 1.00E−06 |
| RNA Pol 1 Promoter Opening | Up-Regulated | 2 | 1.00E−06 |
| Amyloids | Up-Regulated | 3 | 1.00E−06 |
| Packaging of Telomere Ends | Up-Regulated | 4 | 1.00E−06 |
| Olfactory Signaling Pathway | Up-Regulated | 5 | 4.80E−04 |
| Autoimmune Thyroid Disease | Up-Regulated | 6 | 4.00E−04 |
| Asthma | Up-Regulated | 7 | 3.43E−04 |
| Class A1 Rhodopsin Like Receptors | Up-Regulated | 8 | 0.001080874 |
| Immunoregulatory Interactions Between a lymphoid and a non lymphoid Cell | Up-Regulated | 9 | 0.001415851 |
| RNA Pol 1 Transcription | Up-Regulated | 10 | 0.001674173 |
| Cell Cycle Mitotic | Down-Regulated | 1 | 1.00E−06 |
| Mitotic M M G1 Phases | Down-Regulated | 2 | 1.00E−06 |
| Mitotic Prometaphase | Down-Regulated | 3 | 1.00E−06 |
| DNA Replication | Down-Regulated | 4 | 1.00E−06 |
| G2 M Checkpoints | Down-Regulated | 5 | 1.00E−06 |
| Metabolism of Non Coding RNA | Down-Regulated | 6 | 1.00E−06 |

TABLE 3-continued

| GSEA enriched pathway | Regulation | Rank | FDR-corrected (q value) |
|---|---|---|---|
| Activation of the Pre Replicative Complex | Down-Regulated | 7 | 1.00E−06 |
| Cell Cycle | Down-Regulated | 8 | 1.00E−06 |
| Activation of ATR in Response to Replication Stress | Down-Regulated | 9 | 1.00E−06 |
| Cell Cycle Checkpoints | Down-Regulated | 10 | 1.00E−06 |

Interestingly, when the C-MAP database was queried using the gene expression profiling of D425 and D458 medulloblastoma cells after treatment with ALP and PL, it was found that only ALP was able to significantly reverse gene expression as determined by the high positive enrichment score (0.995) and low p-value (p<0.000001).

Discussion

Using the Connectivity Map (C-MAP) algorithm, ALP, a potent inhibitor of CDK1/cyclin B and CDK 5, was identified as a compound with the ability to reverse the gene expression signature of medulloblastomas such as Group 3 medulloblastomas and, thus, exhibited a specific antitumor effect. Results were validated by demonstrating the efficacy of ALP both in in vitro and in vivo models of Group 3 medulloblastoma. ALP effectively decreased cell proliferation and induced apoptosis through AKT pathway blockade. In mouse xenografts of Group 3 medulloblastoma, treatment with ALP significantly reduced tumor growth and improved survival. It was determined that multiple CDK genes (that were upregulated in untreated control medulloblastoma cells) were significantly inhibited in cells treated with alsterpaullone. This supports the notion that the mechanism of action of alsterpaullone is the targeting of CDKs which results in the growth inhibition and apoptosis observed.

PL was the top ranked compound for non-WNT medulloblastomas indicating the ability of this compound to reverse common biological processes in these tumors. Doxorubicin, a well-known chemotherapeutic agent but not used to treat medulloblastoma, was identified as a drug with potential efficacy for both Group 3 and Group 4 tumors.

Relevant portions of references referred to herein are incorporated by reference.

The invention claimed is:

1. A method of treating Group 3 medulloblastoma in a mammal comprising administering to the mammal a paullone compound that is a cyclin-dependent kinase (CDK) inhibitor, wherein the paullone compound is selected from 9-nitro-7,12-dihydroindolo-[3,2-d][I]benzazepin-6(5)-one (alsterpaullone), 9-cyano-I-azapaullone (cazpaullone) or 9-bromo-7,12-dihydro-indolo_,[3,2-d]_,[I]benzazepin-6 (5H)-one (kenpaullone)

2. The method of claim 1, wherein the compound is alsterpaullone.

* * * * *